United States Patent [19]
Chu et al.

[11] Patent Number: 5,770,076
[45] Date of Patent: Jun. 23, 1998

[54] MICROMACHINED CAPSULES HAVING POROUS MEMBRANES AND BULK SUPPORTS

[75] Inventors: Wen-Hwa Chu, Albany; Mauro Ferrari, Lafayette, both of Calif.

[73] Assignee: The Regents of the University of California, Berkeley, Calif.

[21] Appl. No.: 482,237

[22] Filed: Jun. 7, 1995

Related U.S. Application Data

[63] Continuation-in-part of Ser. No. 254,330, Jun. 6, 1994, which is a continuation-in-part of Ser. No. 207,457, Mar. 7, 1994, Pat. No. 5,651,900, and Ser. No. 207,459, Mar. 7, 1994, Pat. No. 5,660,680.

[51] Int. Cl.[6] .............................. B01D 69/10; A61K 9/50; A61K 9/52
[52] U.S. Cl. ........................... 210/490; 216/56; 424/424; 424/451; 604/890.1
[58] Field of Search ........................... 210/321.6, 500.22, 210/500.26, 490; 604/890.1, 891.1, 892.2; 424/421, 424, 425, 451, 456; 216/56, 2

[56] References Cited

U.S. PATENT DOCUMENTS

| | | |
|---|---|---|
| 3,502,455 | 3/1970 | Gardner ...................................... 65/31 |
| 3,556,945 | 1/1971 | Messing . |
| 3,600,147 | 8/1971 | McKinnis et al. ........................... 65/31 |
| 3,791,987 | 2/1974 | Fanger ........................................ 264/4 |
| 3,841,971 | 10/1974 | Messing . |
| 3,845,770 | 11/1974 | Theeuwes et al. ...................... 128/260 |
| 3,936,329 | 2/1976 | Kendall et al. .......................... 437/974 |
| 3,962,052 | 6/1976 | Abbas et al. .......................... 204/129.3 |
| 4,063,271 | 12/1977 | Bean et al. ............................... 357/49 |
| 4,077,885 | 3/1978 | Van Heuven et al. .................. 210/193 |
| 4,078,971 | 3/1978 | Arkles et al. . |
| 4,177,228 | 12/1979 | Prölss ...................................... 264/24 |
| 4,217,898 | 8/1980 | Theeuwes ............................... 128/260 |
| 4,307,507 | 12/1981 | Gray et al. ............................. 437/974 |
| 4,369,565 | 1/1983 | Muramatsu ............................. 29/580 |
| 4,409,331 | 10/1983 | Lim ........................................ 435/178 |
| 4,455,143 | 6/1984 | Theeuwes et al. .................... 604/890.1 |
| 4,473,476 | 9/1984 | McMillan et al. ....................... 210/653 |
| 4,673,566 | 6/1987 | Goosen et al. ........................... 424/19 |
| 4,689,150 | 8/1987 | Abe et al. ............................... 210/490 |
| 4,698,900 | 10/1987 | Esquivel .................................. 457/52 |
| 4,743,545 | 5/1988 | Torobin .................................... 435/41 |
| 4,793,825 | 12/1988 | Benjamin et al. .................... 604/891.1 |

(List continued on next page.)

FOREIGN PATENT DOCUMENTS

| | | |
|---|---|---|
| 292325 | 11/1988 | European Pat. Off. .......... 210/500.22 |
| 1-138110 | 5/1989 | Japan . |
| 1680270 | 9/1991 | U.S.S.R. ............................... 210/506 |
| WO 93/11862 | 6/1993 | WIPO . |
| 93/23154 | 11/1993 | WIPO . |

OTHER PUBLICATIONS

G. Kittilsland et al., "A Sub–Micron Particle Filte in Silicon," *Sensors and Actuators*, A21–A23, (1990), pp. 904–907.

W. Lang et al., "Application of Porous Silicon as a Sacrificial Layer," *7th International Conference on Solid–State Sensors and Actuators Digest of Technical Papers*, Jun. 7–10, 1993, pp. 202–205.

*Websters Third New International Dictionary*, Copyright 1986 by Merriam–Webster, Inc., p. 811.

*Primary Examiner*—Joseph W. Drodge
*Attorney, Agent, or Firm*—Fish & Richardson P.C.

[57] ABSTRACT

Surface micromachining and bulk micromachining are employed for realizing a porous membrane with bulk support for a microparticle filter. The filter is sufficiently sturdy to allow for easy handling. It may be used as a diffusion barrier and under high pressures. The disclosed fabrication method is simple, reliable, and integrated-circuit compatible, and thus amenable to mass production. Electronic circuitry may be integrated on the filter surface, as may be desired for several purposes, such as fluid characterization, filter self-cleaning, or charging of the filter surfaces. Methods are shown for the realization of biological containment capsules based on this microfilter.

1 Claim, 25 Drawing Sheets

U.S. PATENT DOCUMENTS

| | | | |
|---|---|---|---|
| 4,797,211 | 1/1989 | Ehrfeld et al. | 210/500.25 |
| 4,814,083 | 3/1989 | Ford et al. | 210/500.25 |
| 4,841,228 | 6/1989 | Zentner et al. | 424/456 |
| 4,851,228 | 7/1989 | Zentner et al. | 424/424 |
| 4,853,001 | 8/1989 | Hammel | 65/31 |
| 4,874,484 | 10/1989 | Foell et al. | 204/129.3 |
| 4,937,209 | 6/1990 | Jones et al. | 501/80 |
| 4,981,590 | 1/1991 | Van 'T Veen et al. | 210/490 |
| 5,126,810 | 6/1992 | Gotou | 357/23.6 |
| 5,131,978 | 7/1992 | O'Neill | 156/653 |
| 5,156,623 | 10/1992 | Hakamatsuka et al. | 604/891.1 |
| 5,160,617 | 11/1992 | Huis Int'l Veld et al. | 210/490 |
| 5,183,607 | 2/1993 | Beall et al. | 264/41 |
| 5,200,334 | 4/1993 | Dunn et al. | 504/12 |
| 5,225,123 | 7/1993 | Torobin | 264/43 |
| 5,230,693 | 7/1993 | Williams et al. | 600/36 |
| 5,234,594 | 8/1993 | Tonucci et al. | 210/500.26 |
| 5,238,613 | 8/1993 | Anderson | 264/22 |
| 5,262,021 | 11/1993 | Lehman et al. | 204/129.55 |
| 5,271,801 | 12/1993 | Valette | 156/653 |
| 5,275,766 | 1/1994 | Gadkaree et al. | 65/31 |
| 5,314,471 | 5/1994 | Brauker et al. | 604/891.1 |
| 5,376,347 | 12/1994 | Ipponmatsu et al. | 423/338 |
| 5,431,921 | 7/1995 | Thombre | 424/424 |
| 5,453,278 | 9/1995 | Chan et al. | 424/424 |
| 5,585,011 | 12/1996 | Saaski et al. | 216/56 |
| 5,603,953 | 2/1997 | Herbig et al. | 424/451 |
| 5,645,684 | 7/1997 | Keller | 216/2 |
| 5,651,900 | 7/1997 | Keller et al. | 210/500.26 |
| 5,660,680 | 8/1997 | Keller | 216/2 |

MICROMACHINED CAPSULES HAVING POROUS MEMBRANES AND BULK SUPPORTS

CROSS REFERENCE TO RELATED APPLICATIONS

This application is a continuation-in-part of U.S. Pat. application Ser. No. 08/254,330 filed Jun. 6, 1994 which is a continuation-in-part of U.S. patent application Ser. No. 08/207,457 filed Mar. 7, 1994, now U.S. Pat. No. 5,651,900, and a continuation-in-part of U.S. pat. application Ser. No. 08/207,459 filed Mar. 7, 1994, now Pat. No. 5,660,680. The entire disclosures of these applications are incorporated herein by reference.

BACKGROUND OF THE INVENTION

The present invention relates generally to microfabricated porous membranes with bulk support, and more particularly to microfabricated porous membranes whose bulk support is an unetched portion of a substrate on which the membrane was fabricated.

Porous membranes may be used as elements of absolute particle filters, immunological barrier capsules and time-release diffusion barriers. Devices incorporating porous membranes must have sufficient mechanical strength to withstand routine handling during fabrication and use. These devices must also be able to withstand the mechanical stresses inherent in their intended use.

Filtration devices are an indispensable necessity, for example, of current health care technology, and in particular of biotechnology. Within the health care industry, examples of areas that require accurate filtration devices are patient and blood product protection, diagnostics, and the fields of pharmaceutical, biotechnology and bioprocessing, including blood fragmentation technology. For several applications within these domains, required filter features include: control of the pore sizes and distributions, and of the relative diffusion rates; absolute pore sizes as small as the nanometer range; high durability; and biochemical and mechanical resistance. Certain existing, commercially-significant filter technology employs polymeric membranes, and is incapable of addressing a variety of needs in the cited application areas.

Precise control of filter pore sizes in the 50 to 100 angstrom range, for either organic or inorganic filters, would allow, for example, biologically important molecules to be mechanically separated on the basis of size. In the present state of the art, there is a very limited selection of filters having pores much less than the resolution limit of 0.35 microns of photolithography. Some filters known heretofore having pore sizes in this range include polycarbonate membrane filters, sintered filters, zeolites, and one instance of a microfabricated bulk micromachined filter.

Polycarbonate membrane filters (nucleopore filters) may be used where pore sizes between 500 and 3500 angstroms are needed. These filters, however, cannot be used at high temperatures, in strong organic solvents, or where no extracted oligomers can be tolerated. The pores of polycarbonate membrane filters are also randomly located. As such, there is a compromise between having a high enough population of pores per unit area and having too many instances of partially overlapping pores. Partially overlapping pores provide pathways through the filter that allow some particles to get through that are larger in diameter than the rated cut-off size of the filter.

Filters that are available in other materials, such as metals or ceramics, are made by sintering together discrete particles. This technique yields a random structure with a relatively large dead volume and no exact cut-off size above which transport is impossible.

Materials such as zeolites, which have a crystal structure with large channels, can be used as molecular sieves in the limited range of from about 5 to 50 angstroms. Zeolites are not amenable to fabrication as thin membranes.

A microfabricated filter with bulk micromachined structures is described by Kittilsland in *Sensors and Actuators*, A21–A23 (1990) pp. 904–907. This design uses a special property of silicon wherein silicon becomes resistant to a certain etchant when highly doped with boron. The pore length of this filter is determined by the lateral diffusion of boron from a surface source at a single crystal silicon-thermal oxide interface. As is known, such lateral diffusion is the diffusion in the plane of the source, away from the source. The use of this technique makes it very difficult to precisely control the pore length. Also the method of fabricating this filter cannot be applied to materials other than silicon.

Thus, it can be seen that currently there is a need for filters that can be fabricated from a wide variety of materials and that have pores of well controlled shape and size smaller than about 3500 angstroms and arranged in a precise pattern to exclude the possibility of overlap.

Such pore sizes are also necessary for microencapsulation for immunological isolation. Medical researchers have demonstrated that the concept of microencapsulation to provide immunological isolation is valid. The islets of Langerhans, which produce insulin in mammals as well as hormones that control the metabolism of glucose by other organs, have been transplanted between different species. For example, pig islets have been transplanted into diabetic dogs to control glucose metabolism. However, these unprotected islets function only for a short time before the immune system of the host kills the donor cells.

Encapsulation of islets in order to protect them from immune system macromolecules has been shown to prolong the survival of donor cells. By using various means of encapsulation, insulin production from pig islets has been maintained for over one hundred days in dogs. Encapsulation methods to date include using semipermeable amorphous organic polymeric membranes, sintered together particles, and intermeshed ceramic needles. Significant problems have been encountered, however, limiting the useful life of these capsules to not much more than one hundred days.

The two principal problems with the capsules described above are inadequate mechanical strength and insufficient control of pore size and pore distribution. Specifically, if the thickness of an organic membrane capsule wall is increased to provide the required mechanical strength, molecules cannot diffuse through the capsule wall quickly enough to provide the appropriate physiological response when needed. Moreover, if the size and distribution of pores cannot be controlled, such as with sintered together particles or amorphous polymeric membranes, there is a high probability of oversized or overlapping pores which could provide an opening large enough for immunological macromolecules to enter the capsule.

It is desirable that a capsule combine mechanical strength with the ability to allow the free diffusion of small molecules such as oxygen, water, carbon dioxide, and glucose, while preventing the passage of larger molecules such as the immunoglobins and major histocompatibility (MHC) antigens. Also, the intermediate sized molecular products, such as insulin, produced by the donor cells should be able to diffuse out to the host at a sufficient rate to provide the needed metabolic function.

Accordingly, it is an object of the present invention to provide a structure combining mechanical strength with controlled pore size down to the nanometer range.

Another object of the present invention is to provide such a structure obtainable using simple fabrication techniques.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the claims.

SUMMARY OF THE INVENTION

The present invention provides micromachined porous membranes with bulk support and methods for their fabrication.

One embodiment of the method of the present invention includes providing a bulk substrate etchable using a first predetermined etching process, and forming a thin film etch-stop over a first area of a first surface of the bulk substrate. The etch-stop is etchable using a second predetermined etching process and is not etchable using the first predetermined etching process. Next, the method involves forming at least part of a filter structure over a second area of the first surface, including at least a portion of the first area. The filter structure is not etchable by the second predetermined etching process. A portion of the bulk substrate underneath the thin film etch-stop is ethched using the first predetermined etching process beginning at a second surface of the bulk substrate, and at least a portion of the thin film etch-stop is etched using the second predetermined etching process.

Another embodiment of the method of the present invention includes providing a bulk substrate etchable using a predetermined etching process and forming at least part of a filter structure over an area of a first surface of the bulk substrate. The formation of the filter structure includes forming at the first surface a layer unetchable using the predetermined etching process. A thickness of this layer defines at least part of the length of pores of the filter structure. A portion of the bulk substrate underneath the area of the first surface is etched using the predetermined etching process, beginning at a second surface of the bulk substrate.

BRIEF DESCRIPTION OF THE DRAWINGS

The accompanying drawings, which are incorporated in and constitute a part of the specification, schematically illustrate preferred embodiments of the invention and, together with the general description given above and the detailed description of the preferred embodiments given below, serve to explain the principles of the invention.

DESCRIPTION OF THE PREFERRED EMBODIMENTS

Figure 1:
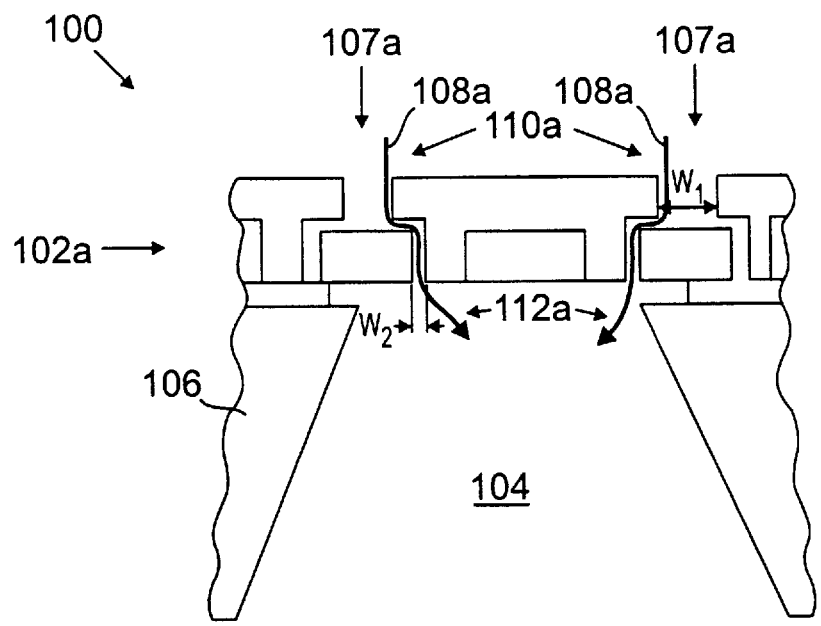
FIG. 1 is a schematic, cross-sectional view of a filter according to the present invention.

The present invention will be described in terms of several preferred embodiments. The preferred embodiments are microfabricated particle filters and containment capsules and methods for their fabrication. A filter 100 according to the present invention is shown in FIG. 1.

Filter 100 includes a porous membrane 102a extending across an opening of a cavity 104 in a bulk substrate 106. Bulk substrate 106 may be monocrystalline silicon, and membrane 102a may be composed of thin-film polysilicon. The paths of flow through pores 107 are indicated by arrows 108a. It should be noted that the flow may also occur in the direction opposite to that of arrows 108a. For the flow direction of arrows 108a, the pores have entrances 110a and exits 112a. Pore entrances 110a are wider than pore exits 112a. The width $W_1$ of entrances 110a are of dimensions permitted by the resolution limit of lithography (greater than about 0.35 microns for photolithography), while the width $W_2$ of exits 112a may be as narrow as a few nanometers. In this sense, the desclosed device provides a multiple-size, sequential filtration apparatus, such as those needed in blood fractionation and other areas of biomedical technology. Filter 100 or parts thereof may be covered by additional coatings (not shown) of inorganic or organic materials, in accordance with specific needs. In particular, metallic coatings such as aluminum, iron, tantalum, or stainless steel may be employed to minimize protein adsorption.

Figure 2:
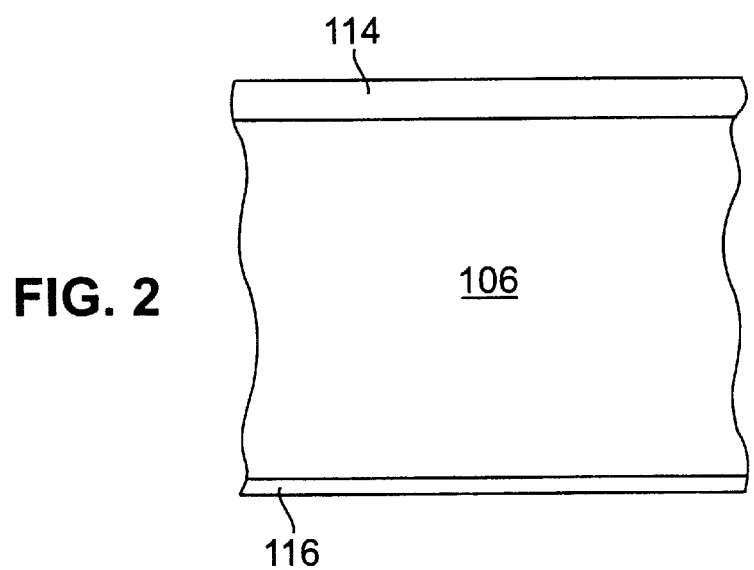
FIGS. 2–10 are schematic, cross-sectional views illustrating steps in the fabrication of the filter of FIG. 1.

Fabrication of the above-described filter may begin with a silicon wafer constituting bulk substrate 106. As shown in FIG. 2, thin films or layers 114 and 116 of silicon dioxide may be thermally grown, on the front and back of the substrate respectively, to a thickness of about 0.58 microns as known in the art. Typical process parameters for this oxidation are 2 hours wet oxidation in pure oxygen at 1000° C.

Figure 3:
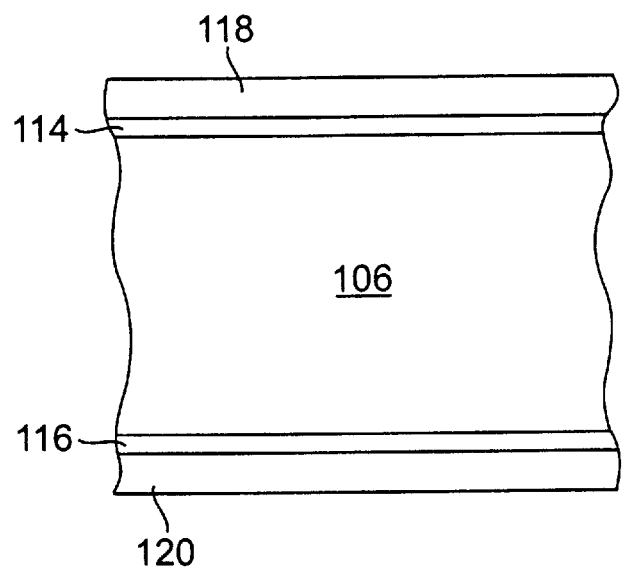
Figure 4:
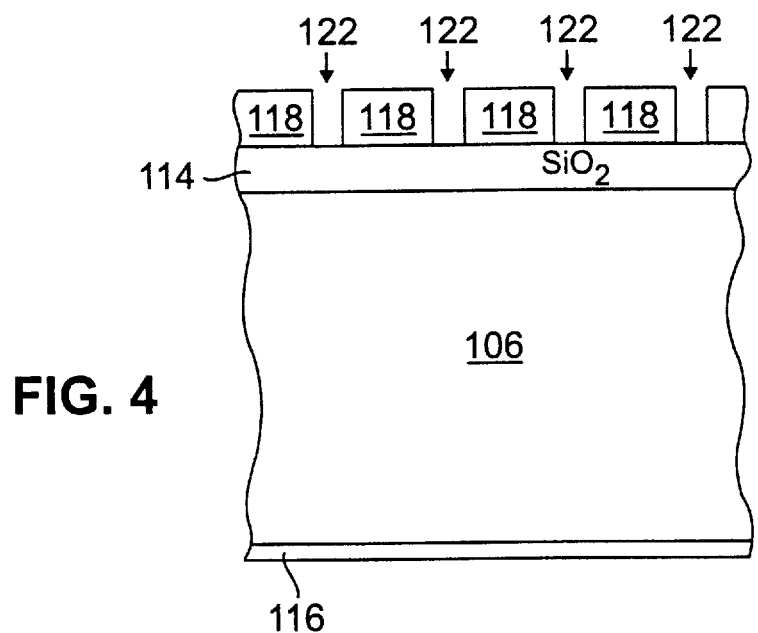

Layers 118 and 120 of polysilicon are then grown on the front and back of the substrate, respectively, as shown in FIG. 3. Layers 118 and 120 may be grown to a thickness of several microns by chemical vapor deposition (CVD), as known in the art. A typical thickness for the layers is three microns. Layer 118 is then patterned using photolithography, as shown in FIG. 4, to form openings 122 whose walls will define the exits 112a of the filtration channel as will be seen from the continued process description below. This patterning may be carried out using a plasma etching process as well known in the art. Typical process parameters are 250 watts of power using chlorine chemistry. Depending on the etching process used, layer 120 may be etched away at the time layer 118 is patterned, or, alternatively, in a subsequent etching step.

Figure 5:
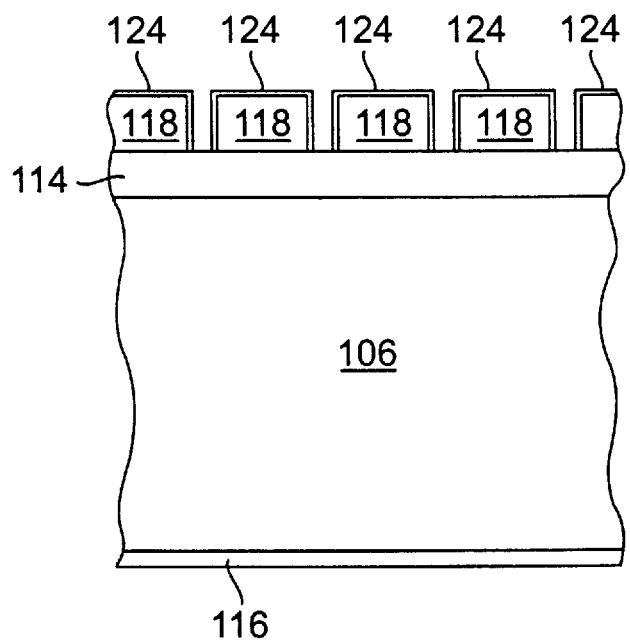

Next, the full wafer is oxidized in a pure (dry) oxygen environment. All exposed polysilicon surfaces will be oxidized, and they will develop a silicon dioxide coating, the thickness of which can be accurately controlled by varying the oxidation parameters such as the oxidation temperature and the oxidation duration, as known in the art. For example, a thickness of 200 angstroms may be obtained by oxidation at a temperature of 900° C. of one hour duration. The configuration following this oxidation step is shown in FIG. 5, where polysilicon 118 is covered by oxide 124. The objective of this oxidation step is to provide a thin layer of well-controlled thickness which may be as low as a few nanometers. As will be shown, subsequent etching of this layer provides the narrow portions of the pores 107a of the device such as pore exits 112a, in accordance with the teaching of above-mentioned patent application Ser. No. 08/207,457 the disclosure of which has been incorporated by reference.

Figure 6:
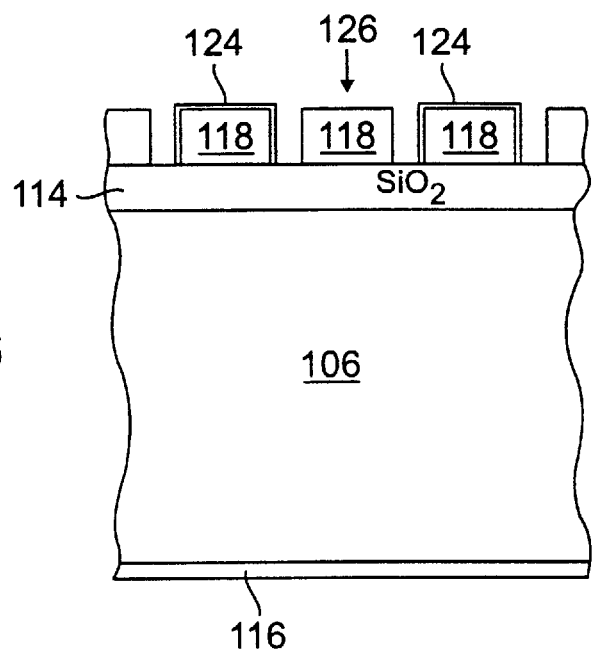

In order to provide anchoring areas for a subsequent polysilicon layer, standard photolithography is used next to remove the thin silicon dioxide 124 from selected areas 126 of polysilicon layer 118, as shown in FIG. 6.

Figure 7:
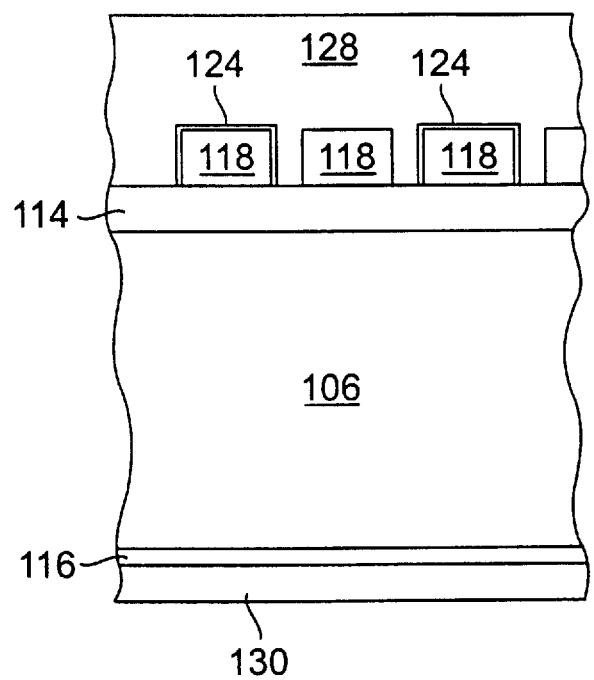

A second layer 128 of polysilicon is then deposited, as described above for layer 118. At the same time, layer 130 of polysilicon is grown on the back side of the wafer. Layer 128 conformally covers the wafer front, and thus fills in openings 122 (FIG. 4) on the wafer surface, as shown in FIG. 7.

Figure 8:
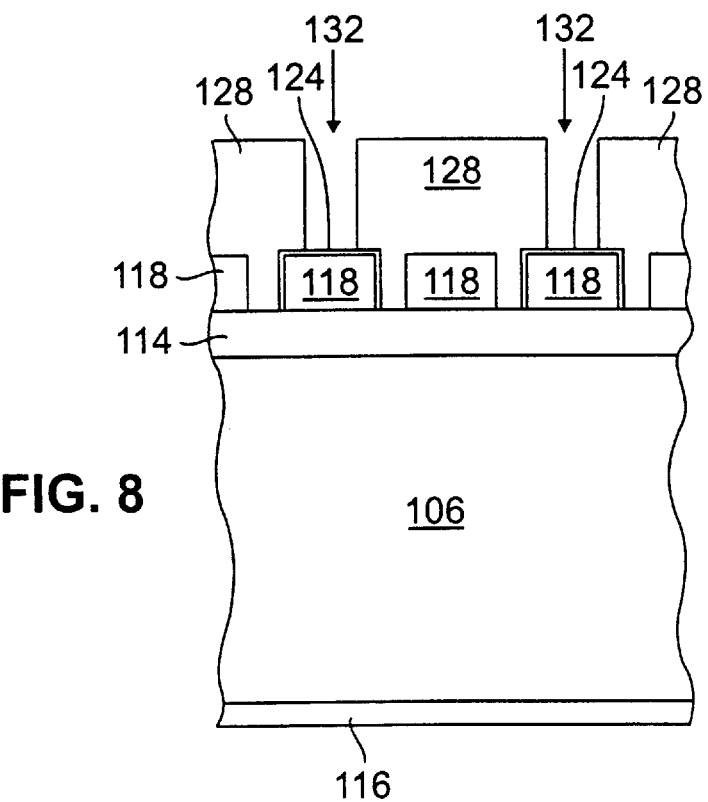

At this point, layer 128 is patterned and holes 132 are produced with standard photolithography as shown in FIG. 8. These holes leave the underlying oxide layer exposed, and constitute pore entrances 110a (FIG. 1). Thus the etching is preferably done by a process that is selective so as not to etch the thin silicon dioxide 124 and the underlying polysilicon layer 118. The same process that was used to etch layer 118 may be used. Holes 132 are not necessarily filtration ports themselves, but are rather intended as passageways for the penetration of the etchant that is to remove oxide 124 and thus create filtration channels. Depending on the etching process used, layer 130 may be etched away at the time layer 128 is patterned, or, alternatively, in a subsequent etching step.

Figure 9:
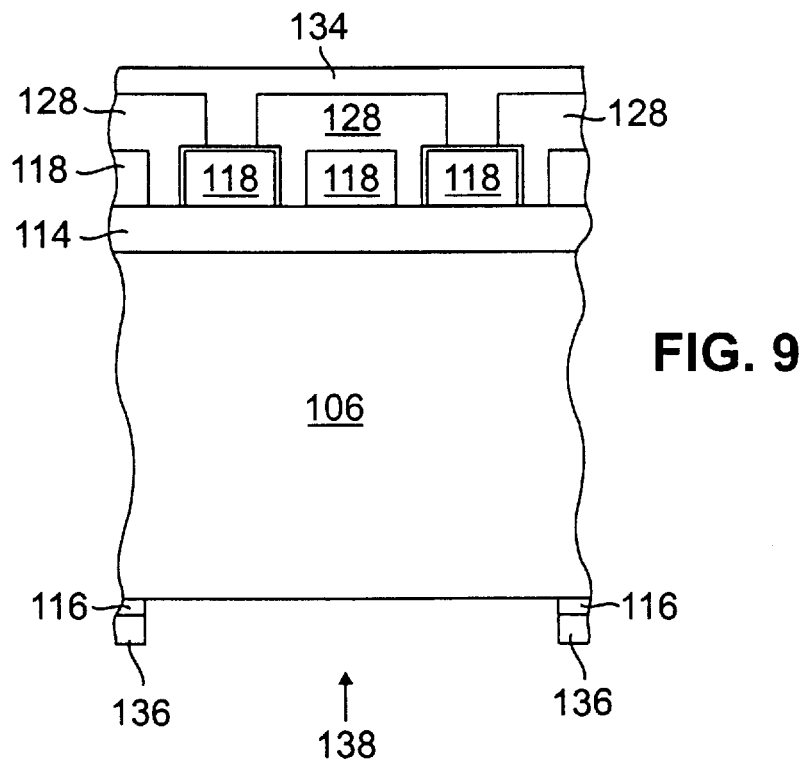

The chemicals used to etch single crystal silicon also attack polysilicon. Therefore, a processing step is necessary to protect the front surface of the wafer during the etching of substrate 106 to provide cavity 104 (FIG. 1). A convenient method for creating a barrier coating is Low Temperature Oxide deposition (LTO). As shown in FIG. 9, LTO is deposited by CVD to cover the front of the wafer with layer 134 and the back with layer 136 (shown in FIG. 9 after the patterning step described below). Standard photolithographic techniques can now be used to define the back side etching window 138 in oxide layers 116 and 138 (FIG. 9).

Figure 10:
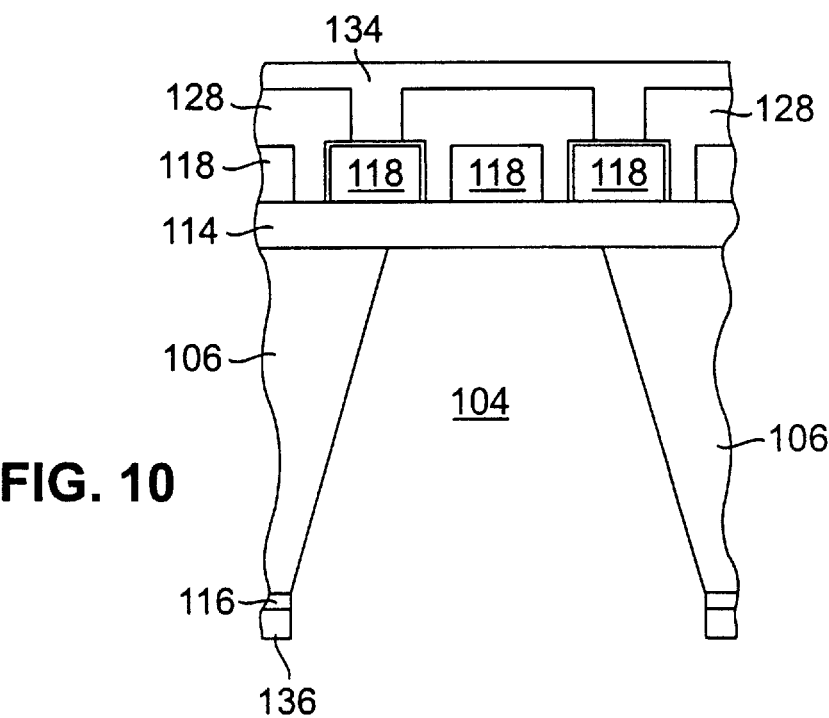

Next, cavity 104 (FIGS. 1, 10) is etched in substrate 106 using layers 116 and 136 as a mask. For low undercut during the etching of the thick substrate and high selectivity with respect to etch-stop oxide layer 114, anisotropic wet etching may be used for single crystal silicon substrates, as known in the art. For example, EDP etchant may be used. As is known, EDP consists of a combination, for example, of 1000 g ethylenediamine, 320 g water, 320 g pyrocathecol and 6 g of pyrazine.

The substrate etching process automatically stops at the silicon dioxide etch stop layer 114 since silicon dioxide is not attacked by EDP significantly. At this point, the device is ready for the final processing step, the removal of the etch stop layers 134, 114, 116 and 136, and of the pore definition sacrificial layer 124.

This removal can be achieved by wet etching with hydrofluoric acid (HF). The resulting structure is the previously described structure of FIG. 1.

Figure 11:
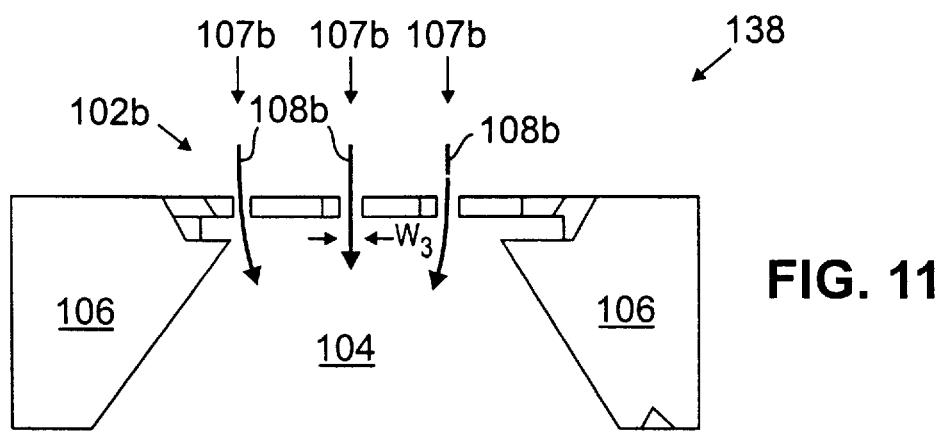
FIG. 11 is a schematic, cross-sectional view of another embodiment of a filter according to the present invention.

A second embodiment with straight-through pores of a filter according to the present invention is filter 138 of FIG. 11. Filter 138 also includes a porous membrane 102b extending across an opening of cavity 104 in bulk substrate 106. Bulk substrate 106 may be monocrystalline silicon, and membrane 102b may be composed of thin-film polysilicon. The paths of flow through the pores 107b are indicated by arrows 108b. It should be noted that the flow may also occur in the direction opposite to that of arrows 108b. The width $W_3$ of the straight-through pores may be as narrow as a few nanometers. As in the case of filter 100, filter 138 or parts thereof may be covered by additional coatings such as aluminum, iron, tantalum, or stainless steel for protein adsorption.

Figure 12:
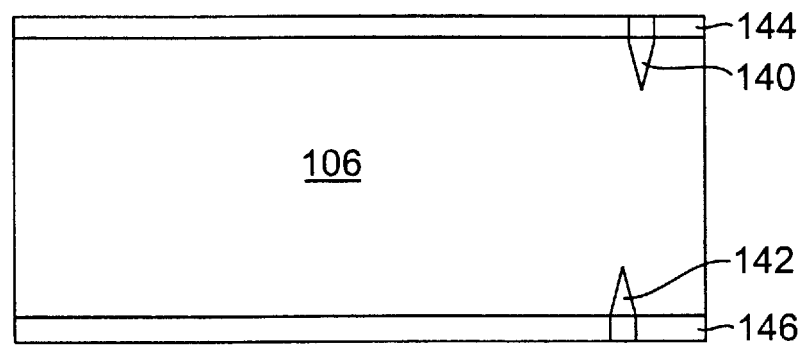
FIGS. 12–22 are schematic, cross-sectional views illustrating steps in the fabrication of the filter of FIG. 11.

As shown in FIG. 12, fabrication of filter 138 begins with the definition of double-sided alignment marks 140 and 142 on the two sides of single crystal silicon wafer 106 covered with silicon dioxide layers 144 and 146. All processes employed in the production of double-sided alignment marks are standard procedures in the field of microelectronic fabrication.

Figure 13:
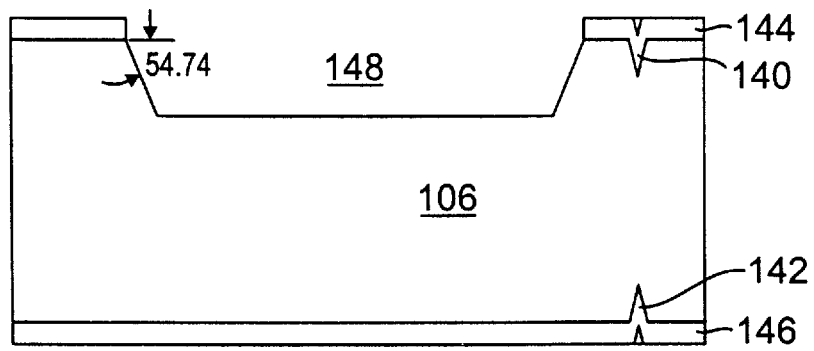

A several micron recess 148 is then generated on the front side of wafer 106 using oxide layer 144 as a mask, as shown in FIG. 13. Silicon anisotropic etching is used to produce this recess as described above for the etching of cavity 104 of filter 100. Because the silicon etch rate along the <100> directions is much faster than along the <111> direction, a 54.74° angle will be generated with respect to the silicon surface as can be seen in FIG. 13.

Figure 14:
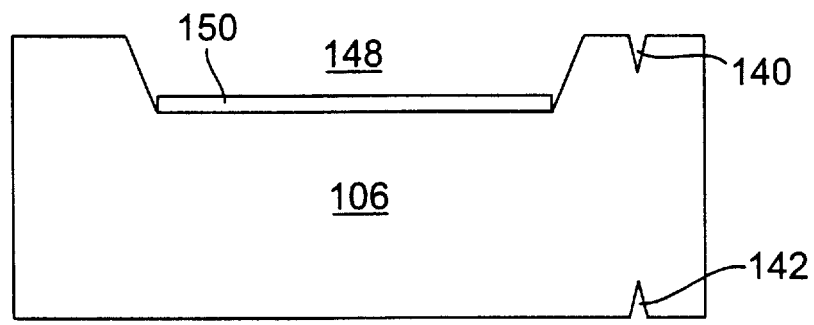

The wafer is further thermally oxidized and the resulting oxide patterned in order to produce a silicon dioxide etch stop pad 150 on the bottom of the recess 148, as shown in FIG. 14.

Figure 15:
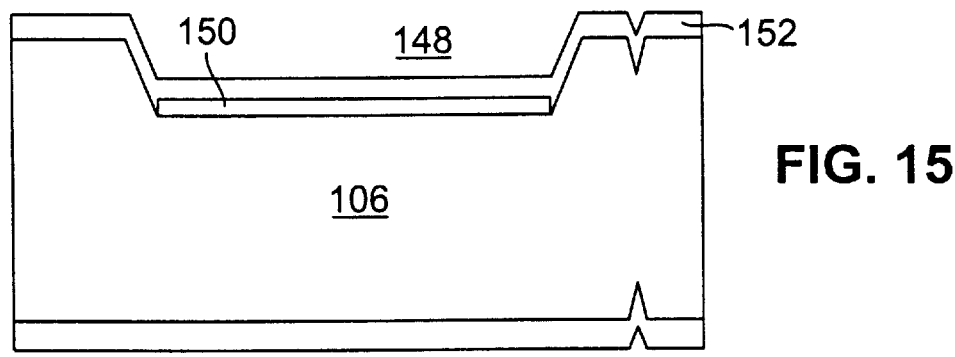
Figure 16:
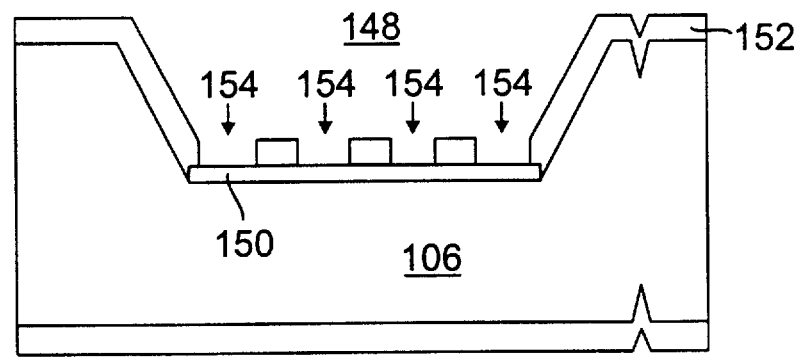
Figure 17:
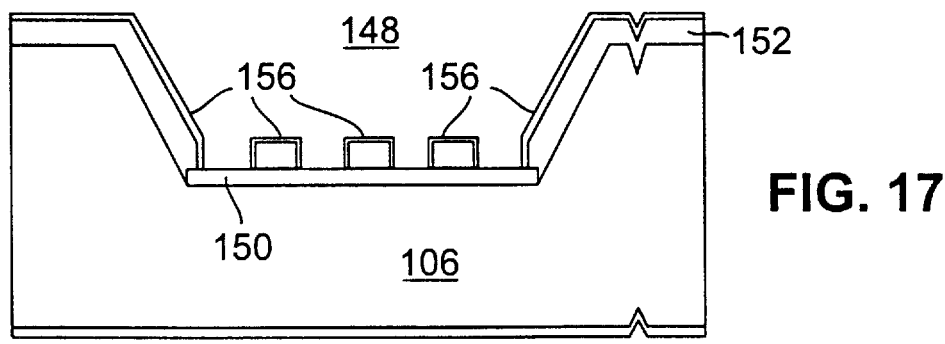
Figure 18:
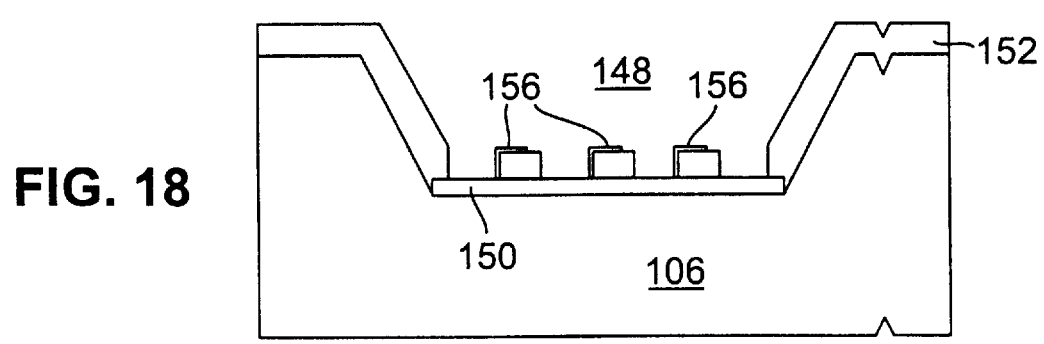
Figure 19:
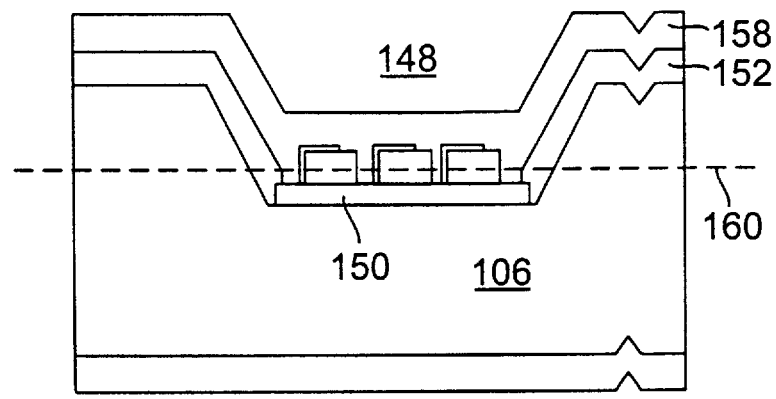

The process steps shown in FIGS. 15–19 are similar to the process steps shown above in FIGS. 3–7. A first layer of polysilicon 152 is deposited as shown in FIG. 15. Layer 152 is then patterned with openings 154 as shown in FIG. 16. The walls of openings 154 establish the location of the pores of the filter. A thin sacrificial silicon dioxide layer 156 is then grown on polysilicon layer 152 (FIG. 17). The thickness of sacrificial layer 156 determines the final pore width. As shown in FIG. 18, photolithography is used to remove silicon dioxide 156 on the sides of recess 148, part of the patterned layer 152, and the portion of layer 152 on the top of wafer 106. The purpose of this removal of silicon dioxide 156 is to open anchor windows for the next polysilicon deposition. A second polysilicon layer 158 is then deposited and anchored to polysilicon layer 152 (FIG. 19).

Figure 20:
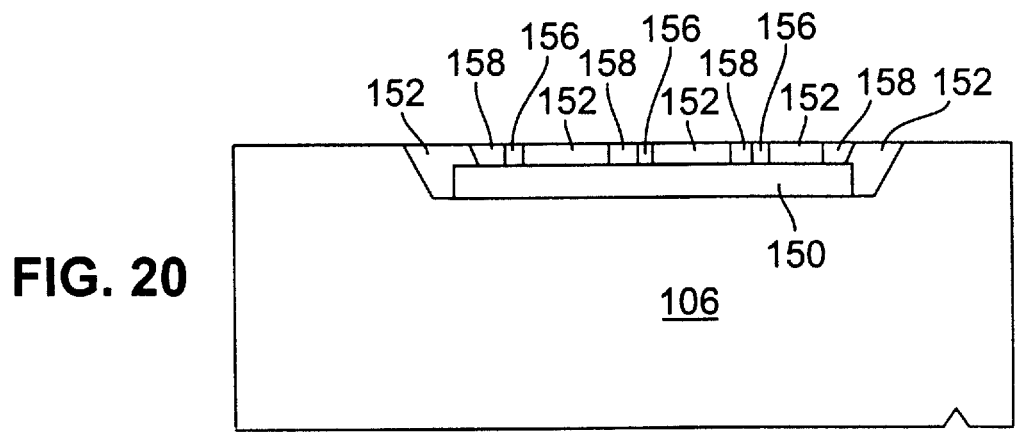

Mechanical lapping and polishing machines can be used to remove unwanted silicon material just above dashed line 160 shown in FIG. 19 so that straight-through pores are obtained. Because of the limited thickness of polysilicon layers 152 and 158, it is not easy to uniformly lap and polish such thin layers. The formation of recess 148 was partially motivated by the fact that a several-micron depth recess in the wafer provides the extra work space for lapping and polishing before operating on the microfilter structures. The resulting structure is shown in FIG. 20.

Figure 21:
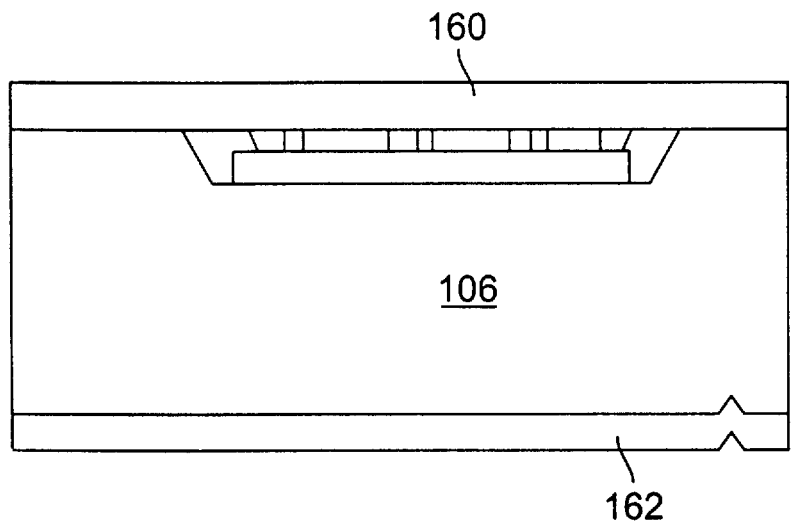

An LTO layer 160 is then deposited on top of the polished wafer and a corresponding LTO layer 162 is simultaneously deposited on the bottom of the wafer as shown in FIG. 21 prior to the silicon substrate anisotropic etching.

Figure 22:
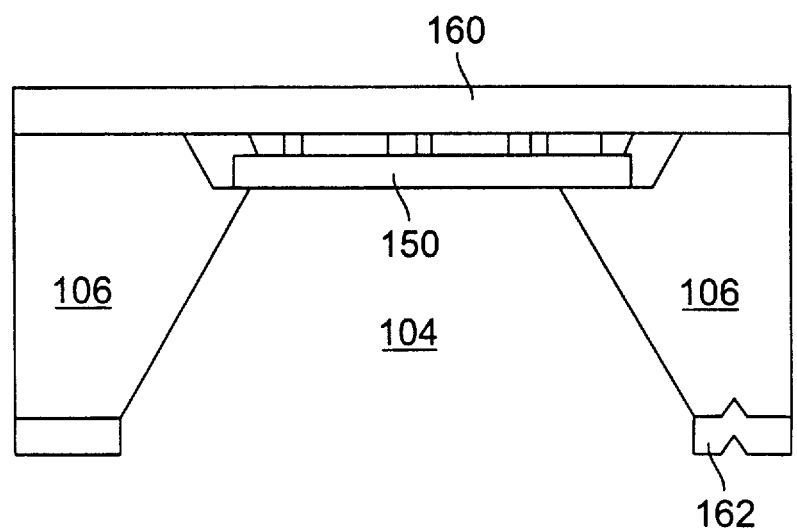

Standard photolithography is then used to define the backside etch windows. The wafer is then etched in a silicon anisotropic etch as described above to produce cavity 104 as shown in FIGS. 22 and 11. Finally wet HF etching is used to remove the silicon dioxide of the etch-stop layers and the pores, resulting in the finished filter shown in FIG. 11.

The etch rate for silicon in certain anisotropic etchants such as ethylinediamine pyrocathecol (EDP) and KOH will decrease drastically if the silicon is heavily boron doped, giving rise to the so-called "p+etch stop" technique for defining etch stops. This technique may be used advantageously in the context of the present invention as taught in the two embodiments described below.

Figure 23:
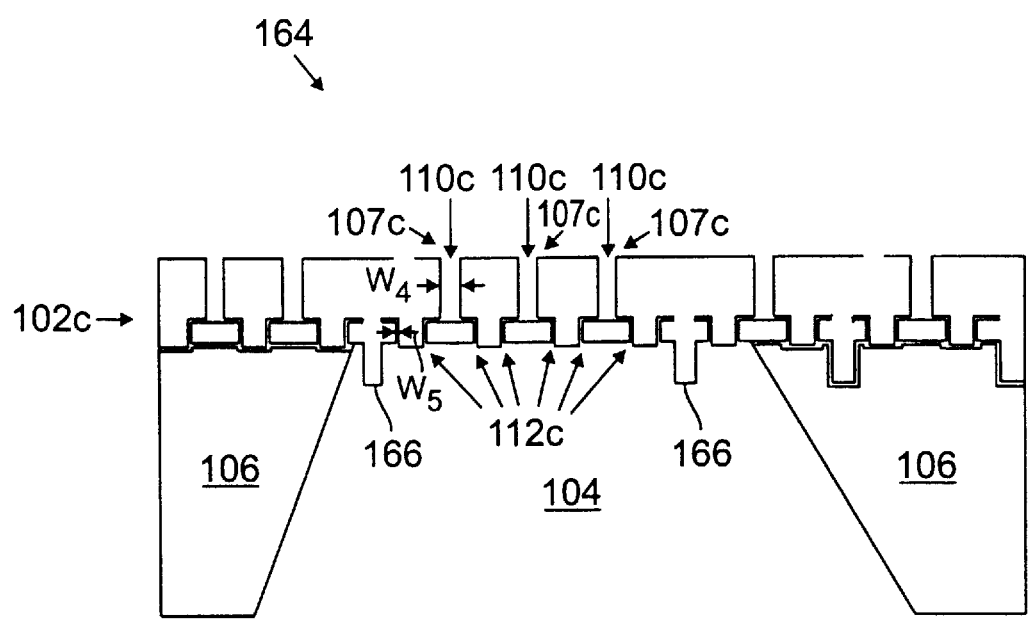
FIG. 23 is a schematic, cross-sectional view of yet another embodiment of a filter according to the present invention.

A third embodiment of the present invention is filter 164 shown in FIG. 23. Filter 164 is similar to filter 100 with the exception of the fact that its porous membrane 102c is heavily boron doped and has reinforcement ribs 166. Porous membrane 102c extends across an opening of a cavity 104 in a bulk substrate 106. Bulk substrate 106 may be monocrystalline silicon. The pores 107c have entrances 110c and exits 112c. Pore entrances 110c are wider than pore exits 112c. The width $W_4$ of entrances 110c are of dimensions permitted by the resolution limit of lithography (greater than about 0.35 microns for photolithography), while the width $W_5$ of exits 112c may be as narrow as a few nanometers. Thus filter 164 provides a multiple-size, sequential filtration apparatus as discussed above. Also as discussed above, filter 164 or parts thereof may be covered by additional coatings such as aluminum, iron, tantalum, or stainless steel.

Figure 24:
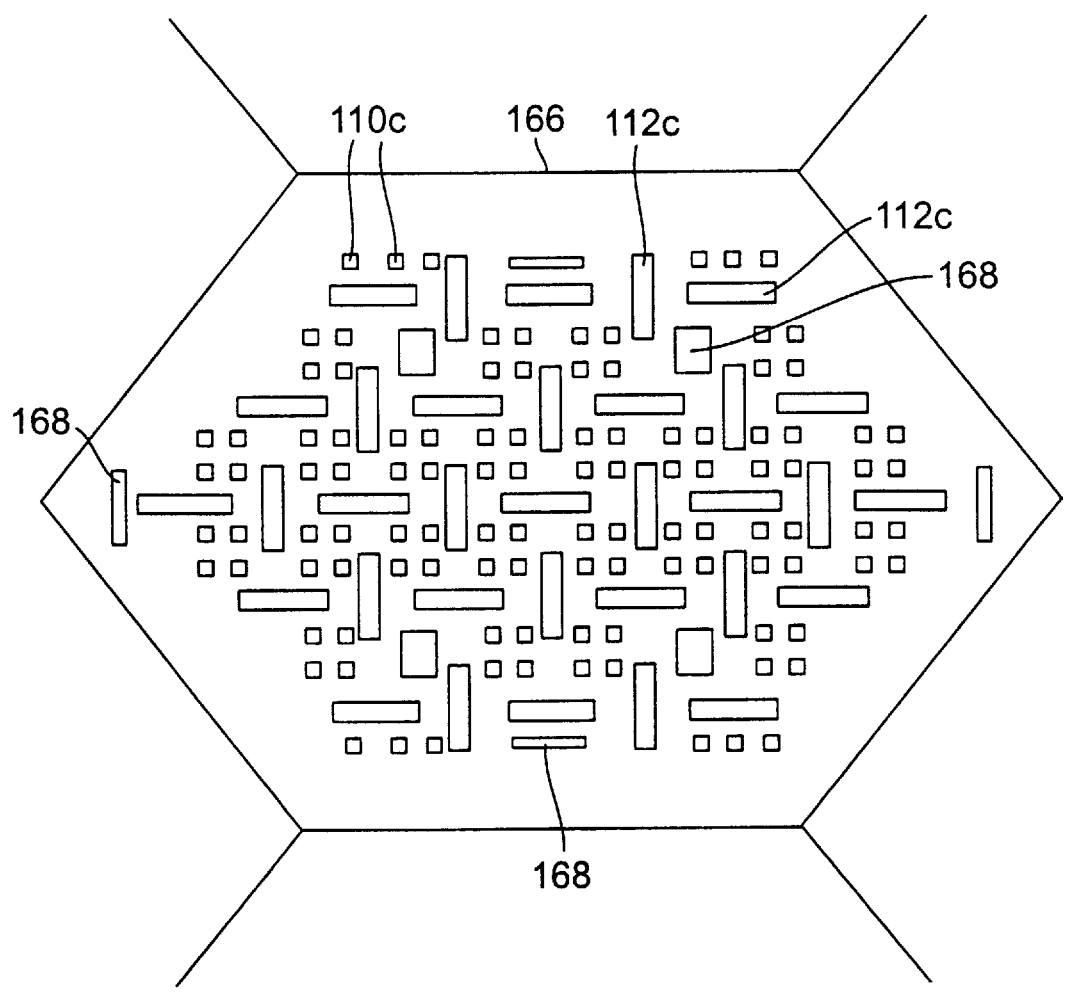
FIG. 24 is a plan view illustrating the layout of the filter of FIG. 23.

FIG. 24 is a plan view of the layout of membrane 102c of filter 164. In addition to the horizontal positions of pore entrances 110c and exits 112c, the horizontal positions of anchoring areas 168 are also shown.

Figure 25:
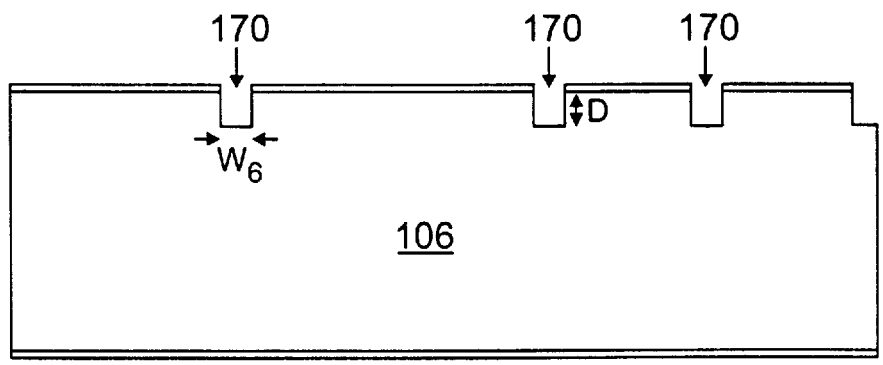
FIGS. 25–35 are schematic, cross-sectional views illustrating steps in the fabrication of the filter of FIG. 23.

Fabrication of filter 164 begins by etching hexagonal reinforcement trenches 170 into wafer 106 using an oxide mask, as shown in FIG. 25. These trenches will be filled with polysilicon in later stages of the process to obtain reinforcement ribs 166, whose purpose is to increase the mechanical strength in the vertical direction of the filtering unit. The typical trench width $W_6$ and depth D are about four and five microns, respectively.

Figure 26:
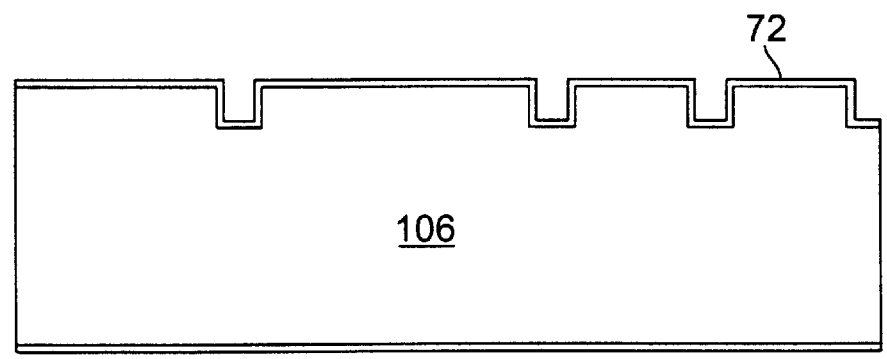

The wafer is then cleaned and wet oxidized as known in the art to get a 3800 angstrom silicon dioxide film 172, shown in FIG. 26. This step is to provide an additional etch stop, as well as a boron diffusion barrier.

Figure 27:
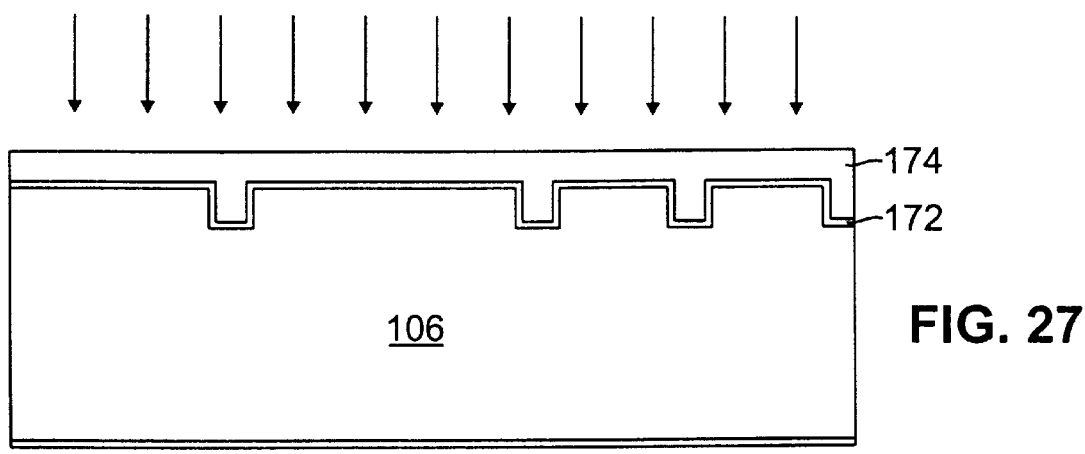
Figure 28:
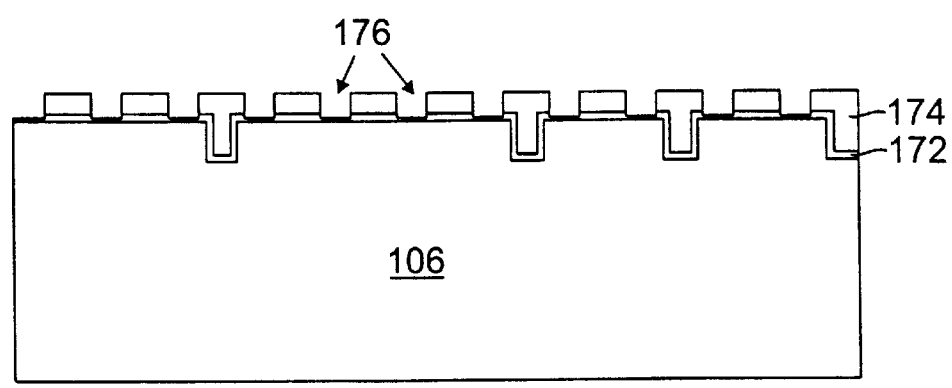

The oxide on the back side of the wafer is then removed. A three micron thick polysilicon film 174 is deposited and subsequently heavily boron doped using solid boron source, as shown in FIG. 27. The concentration of boron in the polysilicon may exceed $5 \times 10^{19}$ per cubic centimeter. Layer 174 is further photolithographically patterned and plasma etched as known in the art to open rectangular openings 176 (FIG. 28), whose walls define the filter pore exits. The polysilicon on the backside of the wafer is removed.

Figure 29:
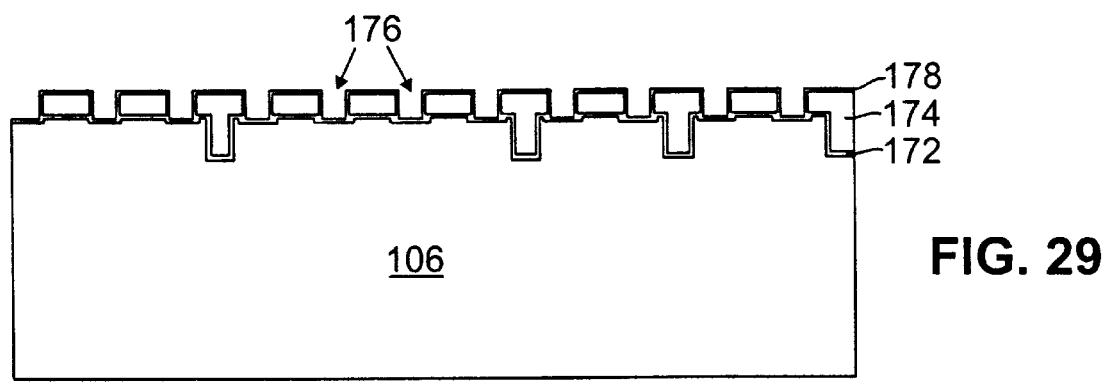

The wafer is cleaned again, and a relatively-low temperature (900° C.) dry oxidation process is used to generate a 200 angstrom thin oxide layer 178 over polysilicon layer 174 (FIG. 29).

Figure 30:
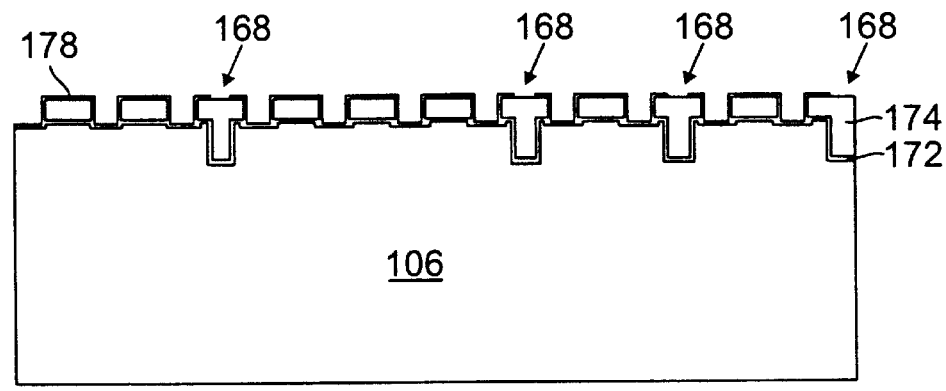

Anchoring openings 168 are then etched in oxide layer 178 as shown in FIG. 30. These openings are used to anchor a subsequent polysilicon layer to polysilicon layer 174.

Figure 31:
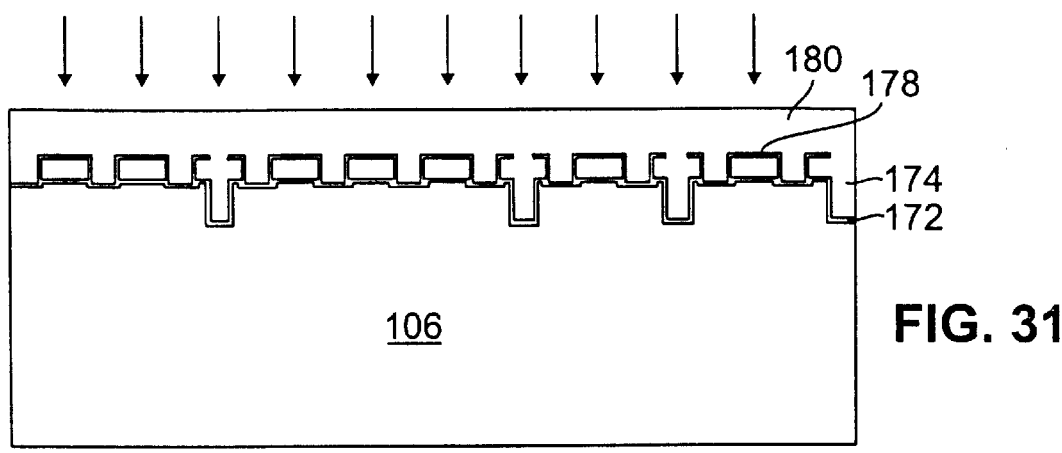
Figure 32:
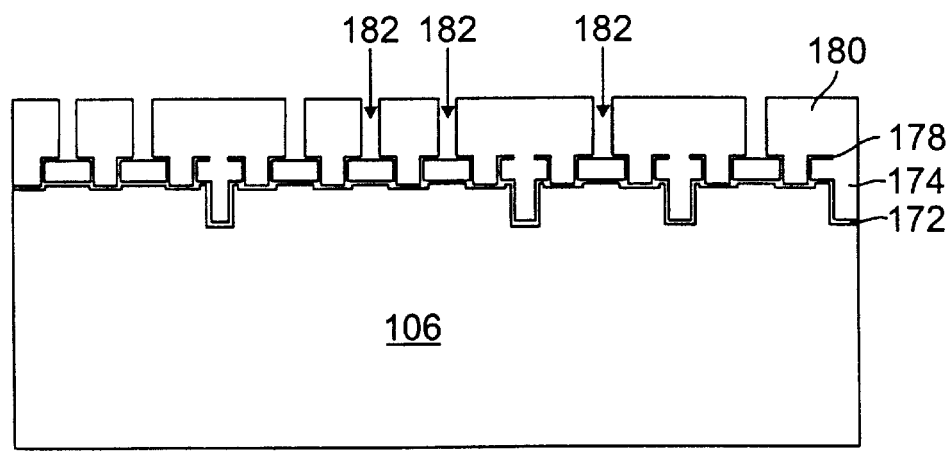

A second polysilicon layer 180 is then deposited and heavily boron doped as can be seen in FIG. 31. Holes 182 are etched in polysilicon layer 180 to expose underlying oxide 178, as shown in FIG. 32.

Figure 33:
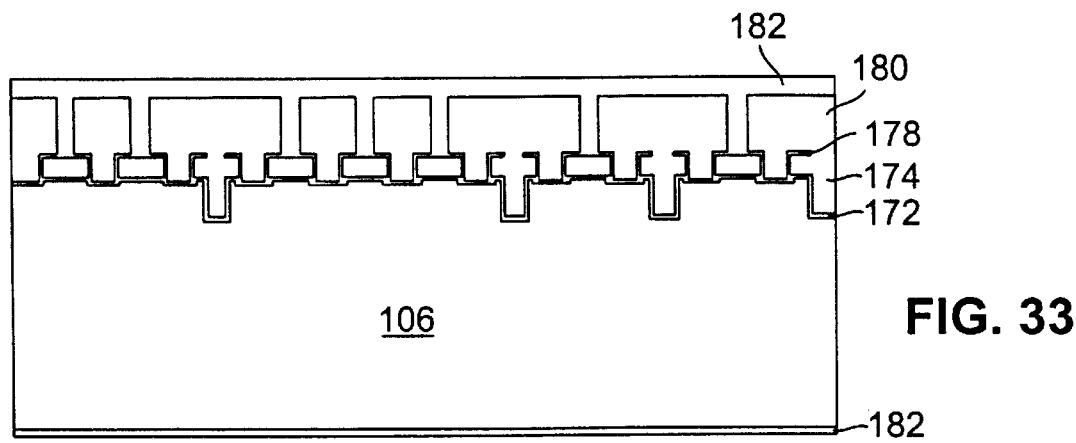
Figure 34:
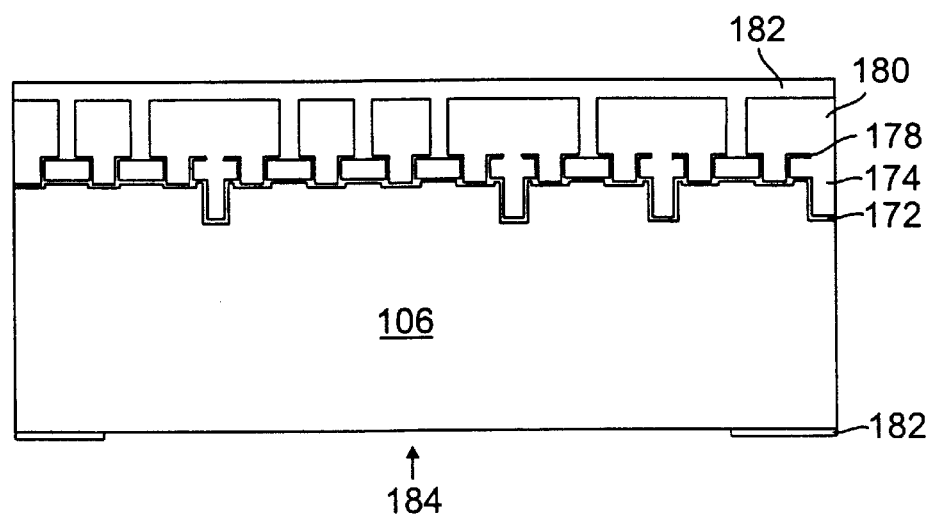

A protective layer of LTO 182 is deposited on both sides of the wafer as shown in FIG. 33, and patterned on the back side to open silicon etching window 184 as shown in FIG. 34.

Figure 35:
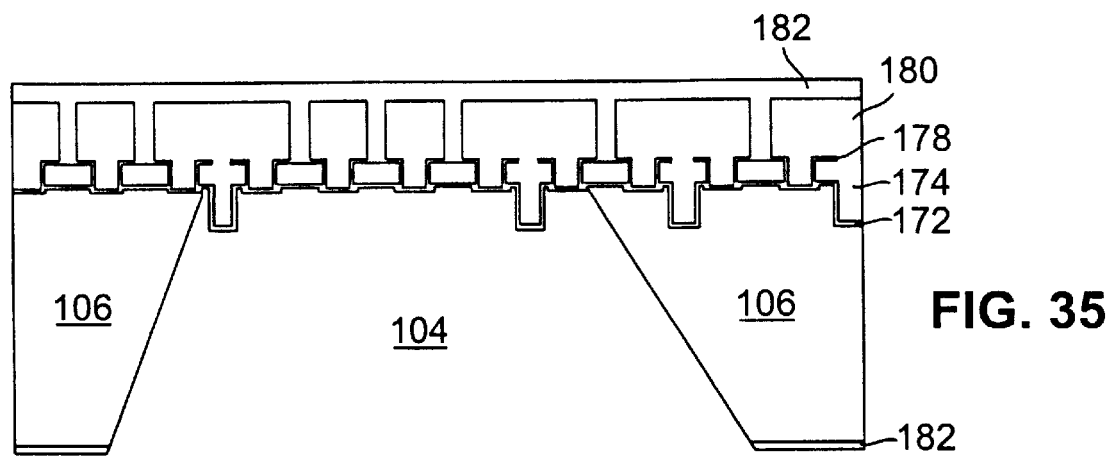

Substrate 106 is then etched using an anisotropic silicon etchant such as EDP resulting in cavity 104, as shown in FIG. 35.

Finally, protective LTO layers 182, pore definition thermal oxide layer 178 and etch-stop thermal oxide layer 172 are etched away using HF, to obtain the filter of FIG. 23.

It is also possible to use the etch-stop characteristics of p+silicon in EDP to reduce the number of fabrication steps described above, by eliminating the deposition of etch-stop oxide layer 172 and of the first polysilicon layer 174. The etching of trenches 170 is also eliminated, as it is not possible to fabricate reinforcement ribs with the process described below. The resulting filter 184, shown in FIG. 36, is similar to the filter of FIG. 23 but without the reinforcement ribs 166.

Figure 36:
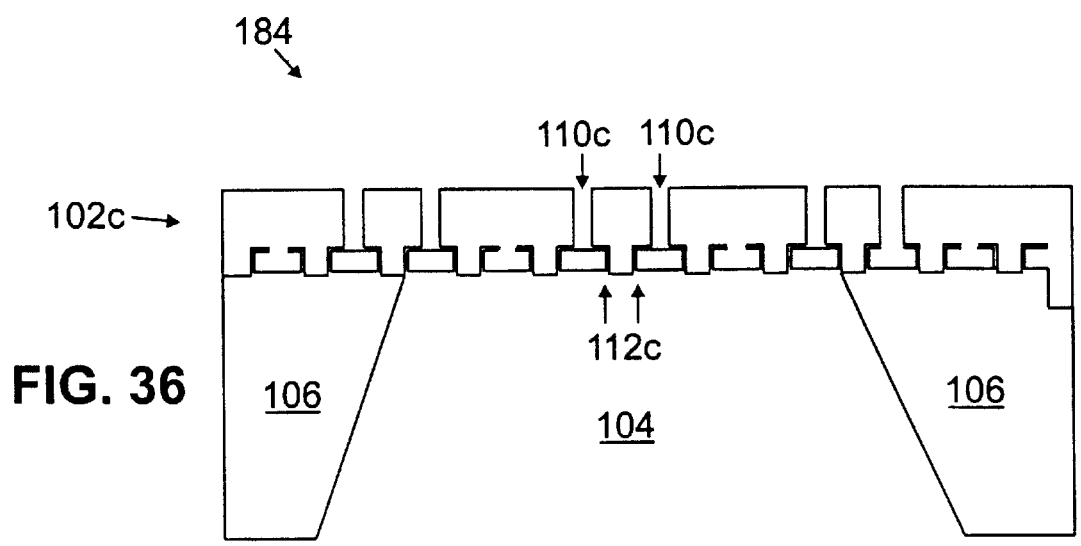
FIG. 36 is a schematic, cross-sectional view of still another embodiment of a filter according to the present invention.
Figure 37:
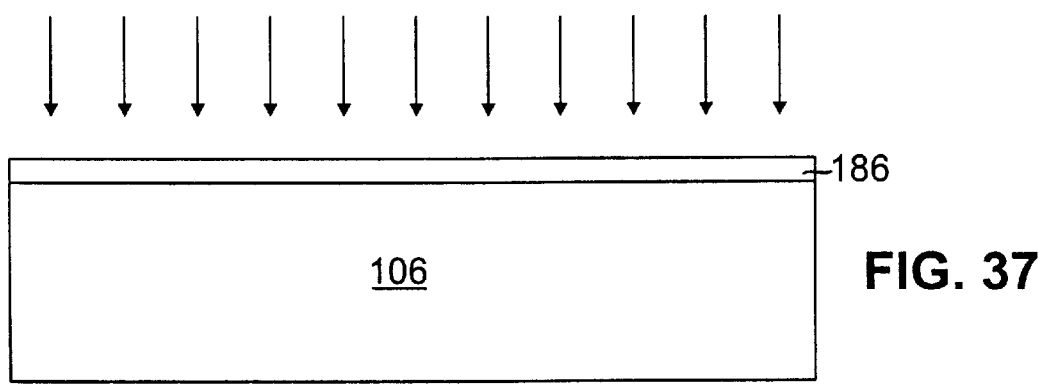
FIGS. 37–45 are schematic, cross-sectional views illustrating steps in the fabrication of the filter of FIG. 36.
Figure 38:
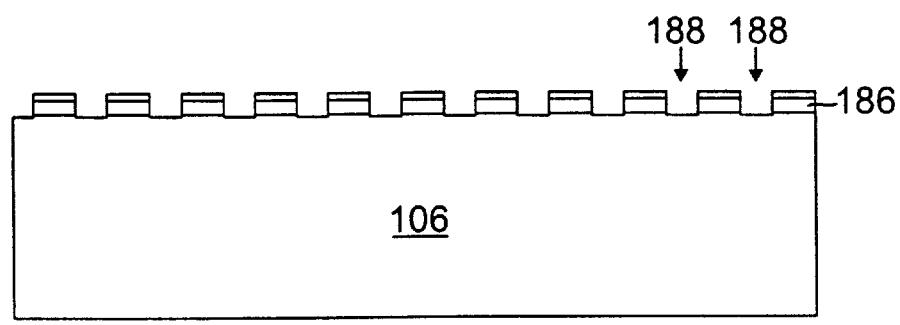

To obtain the filter of FIG. 36, a cleaned silicon wafer is heavily boron doped using a boron solid source, as shown in FIG. 37, to obtain an etch-stop layer 186. The temperature and the diffusion duration will determine how deep the etch-stop 186 will be. Typical values for the depth of the etch-stop are 1–10 microns. The function of this p+etch-stop layer will be similar to that of layer 174 in the embodiment of FIGS. 23–35, and that is to provide part of the filter structure as well as a material to react to generate the thin silicon dioxide layer. Next, this doped p+silicon is patterned and plasma etched as shown in FIG. 38, producing openings 188. The etched depth must be deep enough to penetrate the p+layer so that the filter pores pass all the way through layer 186. The walls of openings 188 define the filter pore exits in the finished filter.

Figure 39:
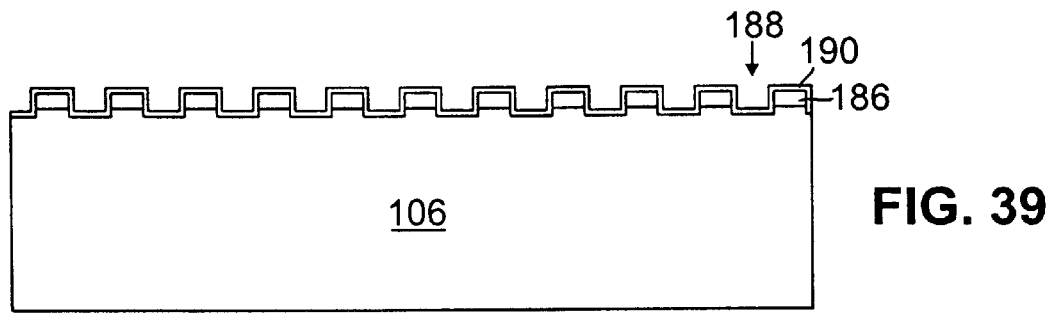

The wafer is cleaned and a relatively low temperature (900° C.) dry oxidation is used to generate a 200 angstrom thin oxide layer 190 over etch-stop layer 186 and substrate 106 (FIG. 39).

Figure 40:
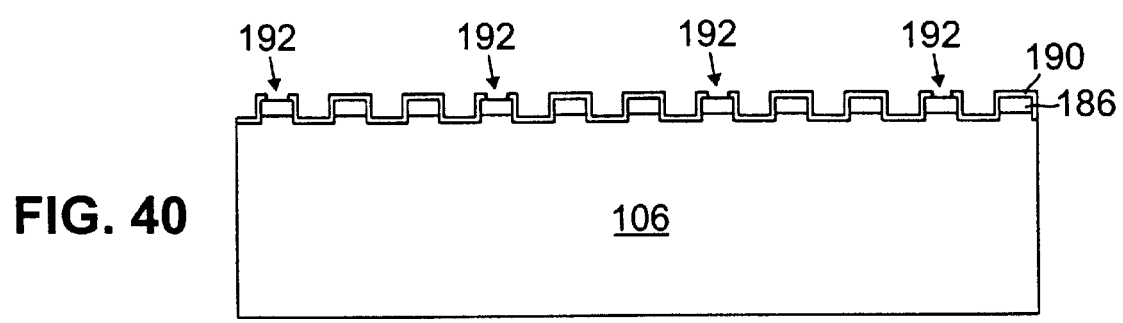

Anchoring openings 192 are then etched in oxide layer 190 as shown in FIG. 40. These openings are used to anchor a subsequent polysilicon layer to etch-stop layer 186.

Figure 41:
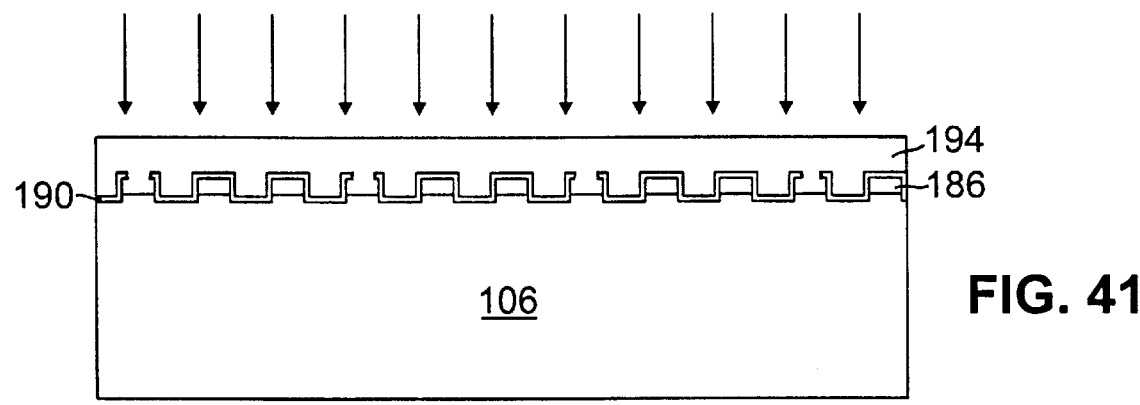
Figure 42:
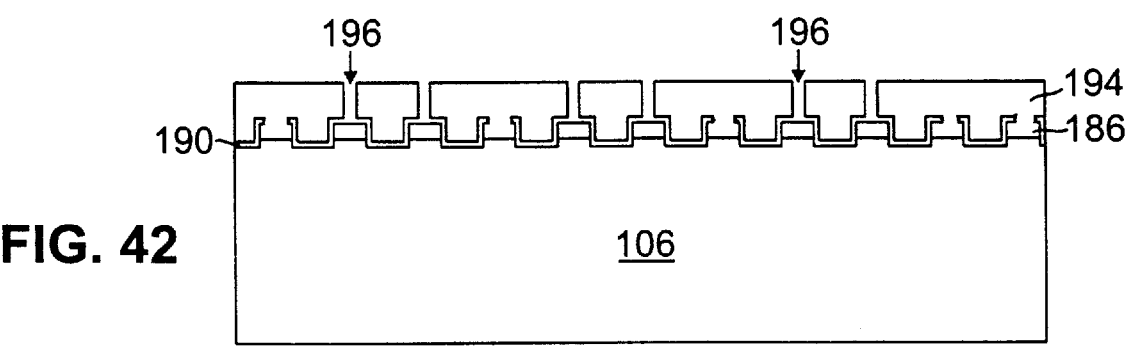

A polysilicon layer 194 is then deposited and heavily boron doped as can be seen in FIG. 41. Holes 196 are etched in polysilicon layer 194 to expose underlying oxide 190 as shown in FIG. 42.

Figure 43:
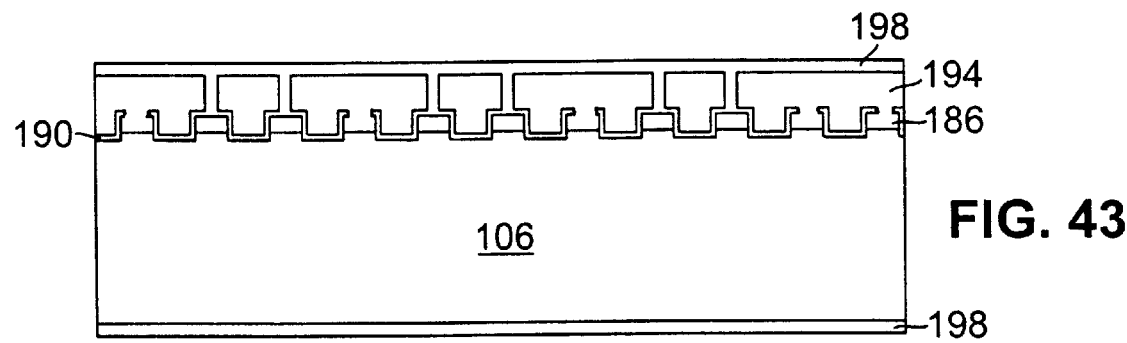
Figure 44:
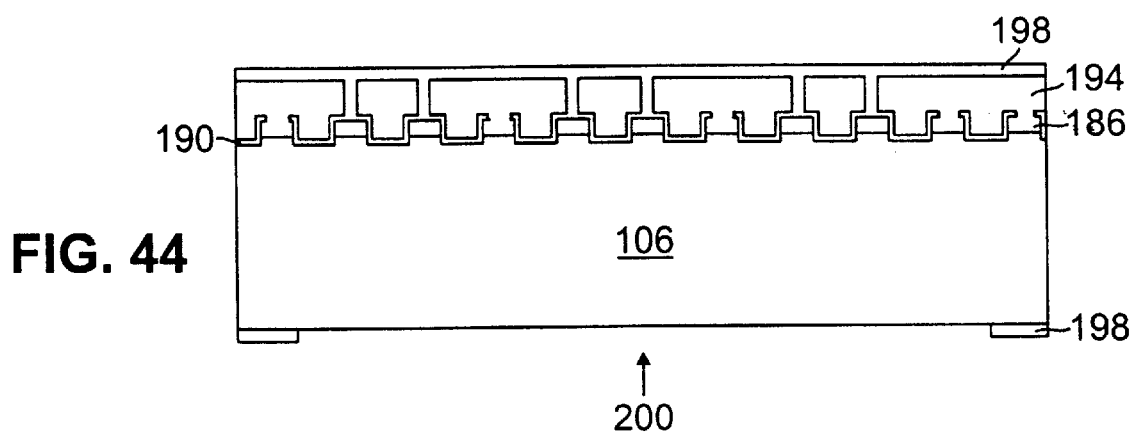

A protective layer of LTO 198 is deposited on both sides of the wafer as shown in FIG. 43, and patterned on the back side to open silicon etching window 200 as shown in FIG. 44.

Figure 45:
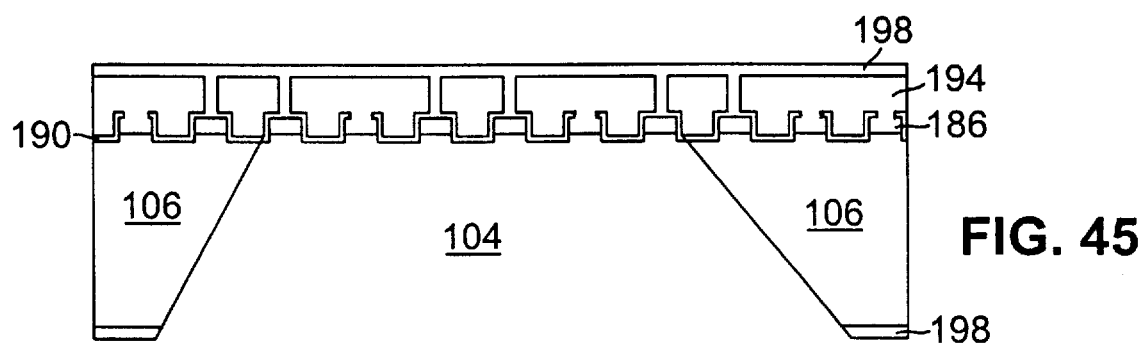

Substrate 106 is then etched using an anisotropic silicon etchant such as EDP resulting in cavity 104, as shown in FIG. 45.

Finally, protective LTO layers 198 and pore definition thermal oxide layer 190 are etched away using HF, to obtain the filter of FIG. 36.

Figure 46:
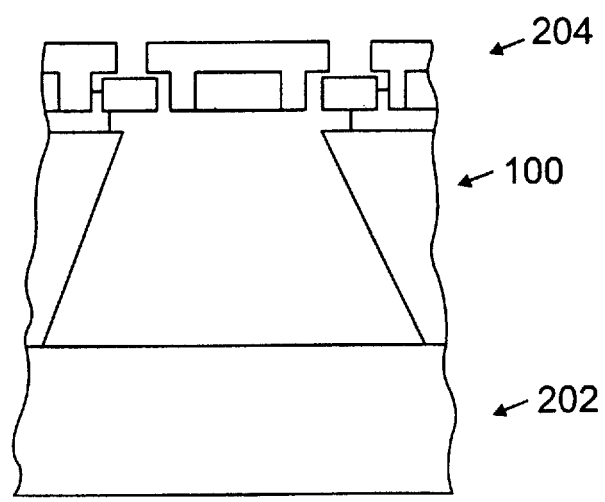
FIG. 46 is a schematic, cross-sectional view of a containment capsule formed using the structure of the filter of FIG. 1.
Figure 47:
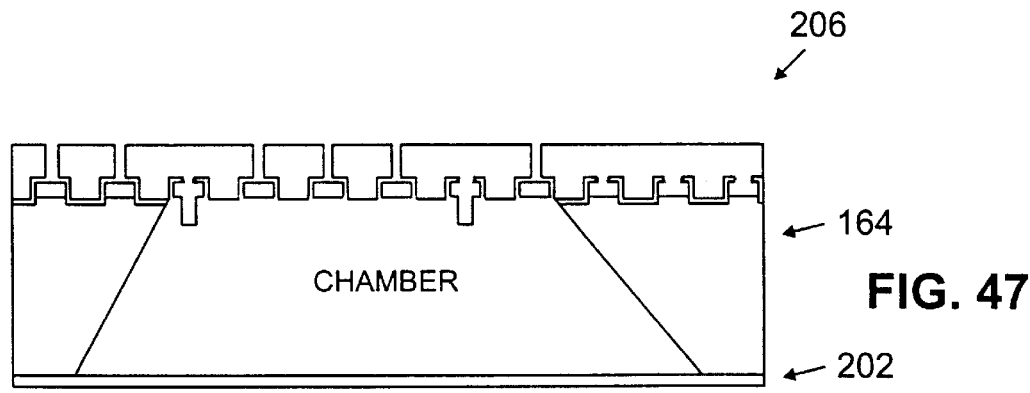
FIG. 47 is a schematic, cross-sectional view of a containment capsule formed using the structure of the filter of FIG. 23.

The above-described filters may be combined with additional filters or non-porous substrates to produce containment capsules usable, for example, for immunological isolation of cell transplants. Such a capsule 204 obtains upon joining a filter such as filter 100 of FIG. 1, or a plurality of such filters integrated on a substrate, to a second wafer 202 at the backside of the filter, as shown in FIG. 46. A similar capsule could be obtained with the filter 138 of FIG. 11, or, as shown in FIG. 47, with filter 164 of FIG. 23. The joining method must be compatible with the material contained in the capsule. Cold pressing and PMMA (polymethyl metacrylate)—or polyethylene-based attachment could be used, and would not damage any biological material contained in the capsule, such as biomolecules, cells or tissue. Similarly, these methods would be appropriate in the encapsulation of pharmacological compounds. Eutectic gold bonding provides an excellent silicon joining method, but could only be used if the temperature involved does not damage the contents of the capsule. A method for filling a capsule with living cells is disclosed in above-mentioned patent application Ser. No. 08/254,330, the disclosure of which has been incorporated by reference.

Figure 48:
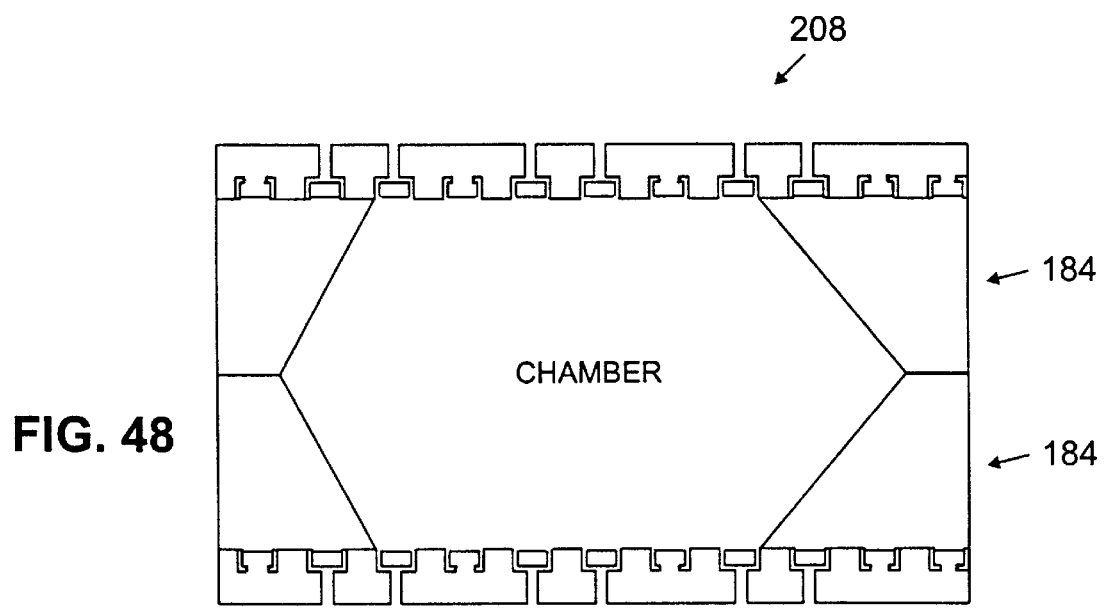
FIG. 48 is a schematic, cross-sectional view of a containment capsule formed using the structure of the filter of FIG. 36.

The wafer joined to the filter may be unprocessed as shown in FIGS. 46 and 47, or bulk processed according to need. For example, the second wafer could be part-way etched to produce a cavity on its front side that is similar to the one on the back side of the filter wafer. Precision alignment of the two wafers, for example by using a jig, and joining would then result in a microcapsule of higher volume. The second wafer could also be bulk and surface processed as described for the fabrication of filters above, to furnish a mirror image of the first one. As shown in FIG. 48 with respect to filter 184 of FIG. 36, precision alignment and joining would then yield a capsule 208 with filtration units on both sides. The filtration units on the two sides need not have the same pore size. In such a case, a filter with multiple barriers would result, each of which deselects particles of different sizes.

In summary, porous membranes with bulk support and methods for their fabrication have been disclosed. As shown, such devices are useful as filters and containment capsules. The filters disclosed are derived from the microfabricated particle filter and microcapsule disclosed in above-mentioned applications Ser. Nos. 08/207,457 and 08/254,330. However, other porous membranes may be employed in conjunction with the disclosed bulk-micromachined reinforcing structures. It may even suffice for certain applications to use photolithographically defined pores. Furthermore, the devices may be integrated with other micromachined devices on the same substrate.

The present invention has been described in terms of a number of preferred embodiments. The invention, however, is not limited to the embodiments depicted and described. Rather, the scope of the invention is defined by the appended claims.

What is claimed is:

1. A microfabricated containment capsule, comprising:

at least one bulk substrate, said at least one bulk substrate delimiting a cavity having a boundary, a first portion of said boundary constituting an inner wall of a solid portion of said at least one bulk substrate; and at a second portion of said boundary, a membrane having at least one porous area with controlled pores and rib members to provide additional structural support to said at least one porous area, providing a selective molecular barrier between an interior and an exterior of said containment capsule.

* * * * *